United States Patent [19]

Daly

[11] 4,234,749

[45] Nov. 18, 1980

[54] CATALYTIC OXIDATION/DECARBONYLATION OF POLYNUCLEAR AROMATIC COMPOUNDS

[75] Inventor: Francis P. Daly, Lawrenceville, N.J.

[73] Assignee: Hydrocarbon Research, Inc., Lawrenceville, N.J.

[21] Appl. No.: 8,305

[22] Filed: Feb. 1, 1979

[51] Int. Cl.³ .......................... C07C 46/00; C07C 4/26
[52] U.S. Cl. .................................. 585/319; 260/385; 585/469; 585/476
[58] Field of Search ............... 585/409, 408, 469, 476, 585/319; 260/385

[56] References Cited

U.S. PATENT DOCUMENTS

| | | | |
|---|---|---|---|
| 2,950,332 | 8/1960 | Mattox | 585/409 |
| 3,062,903 | 11/1962 | Odioso et al. | 585/476 |
| 3,247,263 | 4/1966 | Weidenhammer | 585/469 |
| 3,642,838 | 2/1972 | Caldenazzo | 260/385 |
| 3,725,242 | 4/1973 | Hamner et al. | 208/46 |
| 3,855,252 | 12/1974 | Robinson et al. | 260/385 |
| 3,907,915 | 9/1975 | Chang et al. | 585/408 |
| 3,928,484 | 12/1975 | Suggitt | 585/319 |
| 4,046,825 | 9/1977 | Owen et al. | 585/408 |
| 4,097,541 | 6/1978 | Sakai et al. | 585/319 |
| 4,139,452 | 2/1979 | Beuther | 585/476 |

OTHER PUBLICATIONS

Ho et al., Synthesis, 10, 206, 1972.
Sakai et al., Chem Letters, 617–620, 1974.

*Primary Examiner*—Veronica O'Keefe
*Attorney, Agent, or Firm*—Michael A. Jacobs

[57] ABSTRACT

This invention provides processes for the production of benzene from anthracene, 9,10-anthraquinone from anthracene, and benzene from 9,10-anthraquinone. In the conversion of anthracene to 9,10-anthraquinone, anthracene is reacted with a molecular oxygen-containing gas (e.g., air) in the presence of a catalyst and promotor at an elevated temperature (65° to 205° C.). To convert 9,10-anthraquinone to benzene, the anthraquinone is thermally cracked, with or without a suitable catalyst, at a temperature of at least 425° C. An example of a suitable catalyst is synthetic zeolite.

29 Claims, 4 Drawing Figures

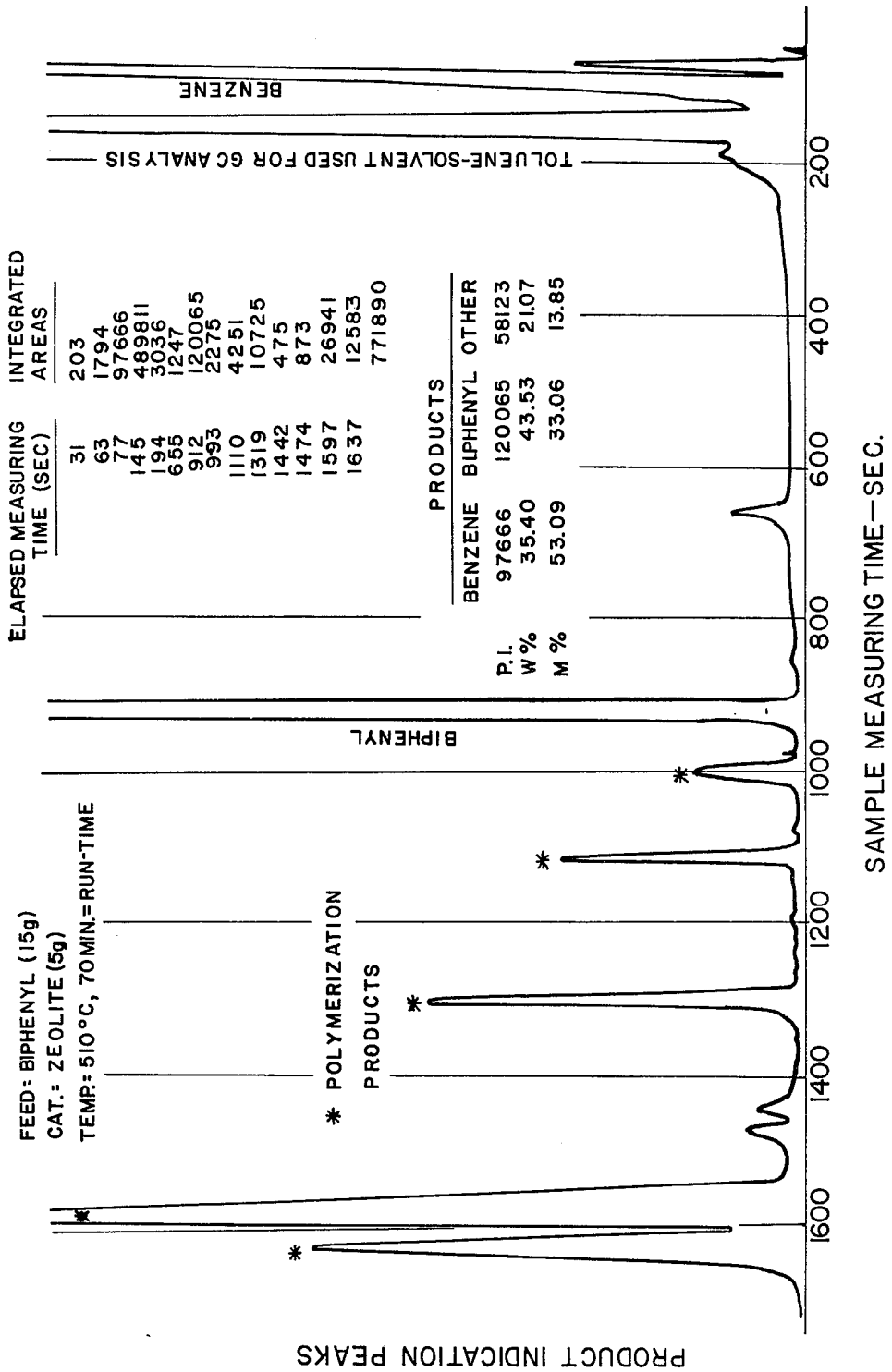

CATALYTIC OXIDATION/DECARBONYLATION OF POLYNUCLEAR AROMATIC COMPOUNDS

BACKGROUND OF THE INVENTION

1. Field of the Invention

This invention relates to a process of converting polynuclear aromatic compounds to mononuclear aromatic compounds. More particularly, this invention is directed to the oxidation of polynuclear aromatic compounds such as anthracene to produce mononuclear aromatic compounds such as benzene.

This invention is also directed to a process for cracking the center ring of polynuclear aromatic compounds.

2. Description of the Prior Art

Polynuclear aromatic compounds such as anthracene, anthracene derivatives, fluorene and fluorene derivatives, and particularly anthracene, have long been valuable items of commerce. These materials are primarily used for preparing oxidized products such as anthraquinone, which is a valuable intermediate in the preparation of stable dyes for the dye industry. While the polynuclear aromatic compounds and the oxidized derivatives thereof can be synthesized from various materials, such synthesis is a very costly source of these compounds. As a result, the primary source of such materials is coal liquids produced by the solvent extraction or destructive dissolution of carbonaceous materials, particularly coal. However, one of the difficulties of recovering these materials from coal liquids is that they are present in such minute quantities that they are difficult to separate from one another and from contaminating materials of substantially similar properties and boiling points.

Although a number of techniques have been suggested for separating anthracene and fluorene from coal liquids, such separations are extremely complex and expensive. This is due to the fact that processes such as fractional crystallization, solvent extraction, and the like, which are expensive, must be used because of the presence of contaminating material in the fraction which reacts and boils similarly.

Additionally, there is a number of processes in the prior art for converting condensed-ring aromatics to their oxidized derivatives, in many cases without separating these compounds from their crude mixtures. However, many of these processes have features which limit their application on a commercial scale.

The conversion of anthracene to anthraquinone in the presence of a catalyst is taught by Ho et al., *Synthesis*, 10,560 (1972). According to this reference, polynuclear aromatic hydrocarbons, such as anthracene, can be oxidized to form 9, 10-anthraquinone, using ceric ammonium nitrate as a catalyst. The reaction is carried out at a temperature of 25° C. This process suffers from the disadvantage that a large amount of the catalyst is consumed as the reaction proceeds, making it necessary to replenish the catalyst supply and thus increasing the cost of the product formed.

The thermal decarbonylation of anthraquinone to biphenyl and then benzene is disclosed by Sakai et al, *Chemistry Letters*, pp 617–620 (1974). According to this reference, the following reaction scheme is taught:

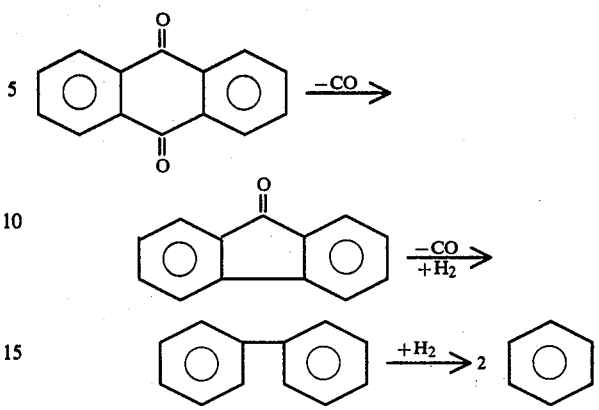

The reaction is conducted in the presence of hydrogen at a temperature from about 800° to 1110° F. The presence of catalysts is not required according to this reference.

The present inventor has discovered that in the oxidation of anthracene to 9, 10-anthraquinone, the catalytic reaction may be substantially improved by conducting the reaction at a temperature of from about 65° to about 205° C. (149°–401° F.) and in the presence of a promoter such as potassium chlorate (KCl O$_3$) and in the absence of water in the reaction system. Under these conditions, the number of moles of anthracene converted per mole of catalyst used is increased several times.

Furthermore, it has also been discovered that by using a catalyst such as zeolite, 9, 10-anthraquinone can be converted to benzene at a temperature of about 425° C. (797° F.) or above without using hydrogen as a reactant. This discovery is significant in that hydrogen is becoming an increasingly expensive feed material. By eliminating hydrogen as a reactant in the conversion of anthraquinone to benzene, the cost of this process is substantially decreased.

SUMMARY OF THE INVENTION

According to the present invention, multi-nuclear aromatic compounds, such as anthracene, may be converted to 9, 10-anthraquinone by contacting the anthracene with a molecular oxygen-containing gas in the presence of a catalyst at suitable temperature and pressure ranges to form anthraquinone and thermally cracking the so-formed anthraquinone, preferably in the presence of a thermal cracking type catalyst, to produce benzene. The process of this invention may be applied to the production of benzene from coal-derived hydrocarbon liquids.

BRIEF DESCRIPTION OF THE DRAWINGS

FIG. 4 illustrates the gas chromatogram results of Example 7.

DETAILED DESCRIPTION OF THE INVENTION

Figure 1:
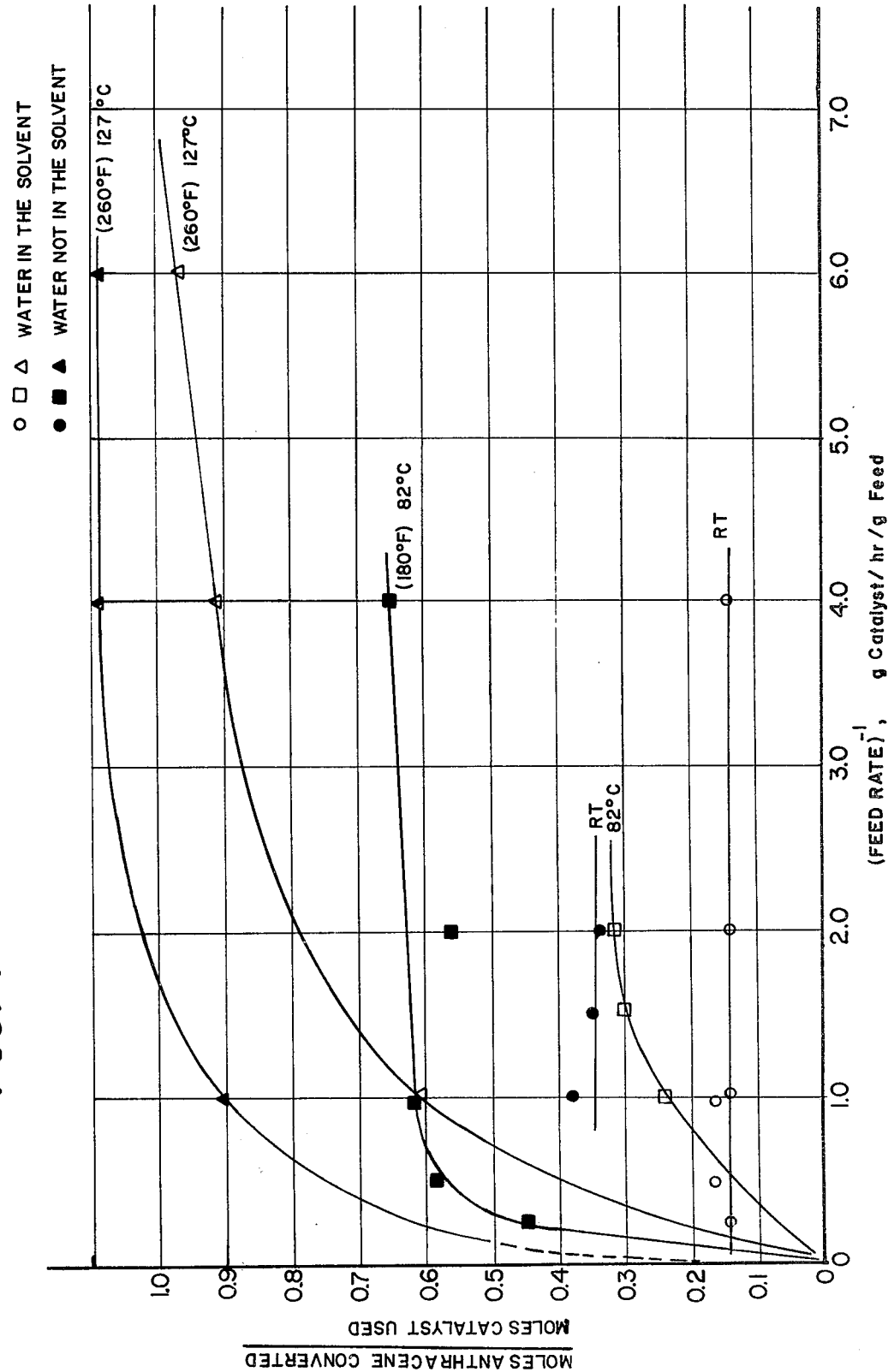
FIG. 1 is a graph of product yields vs reciprocal feed rate which illustrates the results from Examples 1 and 2.

According to the present invention, anthracene is oxidized to 9, 10-anthraquinone (hereinafter anthraquinone) by reacting the anthracene with a molecular oxygen-containing gas in the presence of a catalyst at a temperature of from about 65° to about 205° C. (149°–401° F.), the reaction being carried out in an essentially water-free environment. The so-produced anthraquinone may then be converted to benzene by the thermal cracking thereof in the presence of a thermal cracking type catalyst at a temperature of from about 425° to about 760° C. (797°–1400° F.) and in an inert atmosphere.

Oxidation of Anthracene

In the oxidation of anthracene to anthraquinone, anthracene is reacted with a molecular oxygen-containing gas, such as air, in the presence of a catalyst and a promoter material. Useful catalysts include ceric ammonium nitrate, ceric nitrate, ceric ammonium sulfate, ceric sulfate and ceric perchlorate, with ceric ammonium nitrate being preferred. Useful promoters include potassium chlorate, sodium chlorate and lithuim chlorate, with potassium chlorate being preferred. The oxidation is usually conducted at a temperature of from about 65° to about 205° C. (149°–401° F.), preferably from about 82° to about 150° C. (180°–302° F.). This temperature range is sufficient to permit adequate regeneration of the catalyst without being high enough to cause catalyst decomposition. To obtain better results, the reaction should be carried out in an essentially water-free environment, i.e., the reaction system should not contain water exceeding 1–2 weight percent.

In this oxidation step, it is important that the temperature be within the above mentioned range. It has been found that by maintaining the oxidation reaction temperature within the above mentioned range, the number of moles of anthracene converted per mole of catalyst used is from about 2 to about 10 times greater than that obtained at room temperature. Furthermore, by maintaining a water-free reaction system, the number of moles of anthracene converted per mole of catalyst used is from about 4 to about 16 times greater than that when water is included in the reaction system.

Oxidation of anthracene in a water-free system at elevated temperatures promotes the isomerization of 9, 10-anthraquinone to an unknown product labeled x, y-anthraquinone. It has been found that this isomerization can be significantly reduced by adding a promoter such as potassium chlorate to the reaction system. The yield of x, y-anthraquinone was found to decrease to approximately 1 mole percent when the weight ratio of potassium chlorate to catalyst reached approximately 0.5.

As the starting material in the oxidation reaction, anthracene alone may be used. Alternatively, the anthracene may be admixed with other hydrocarbon liquids. Examples of such admixture of anthracene and hydrocarbon liquids include coal liquids boiling between about 170° to about 380° C. (338°–716° F.) such as anthracene, anthracene derivatives, phenanthrene, phenanthrene derivatives, fluorene and fluorene derivatives. Thus, the above oxidation step which is useful in oxidizing anthracene to anthraquinone is also useful as one of the steps in converting the anthracene present in coal liquids having a boiling temperature ranging from about 170° to about 380° C. to anthraquinone. The so-obtained anthraquinone may be separated from the admixture of reaction products and recovered as a final product. Alternatively, the anthraquinone may be further converted, either after being separated from the liquid mixture or while present in the reaction mixture, to form benzene.

The oxidation of the antracene may be carried out at a gravimetric feed rate of from about 0.2 to about 2.5 gram anthracene/hour/grams catalyst, with from about 0.25 to about 1.00 gram anthracene/hour/grams catalyst being preferred.

Catalytic Cracking of Anthraquinone

The anthraquinone obtained by the oxidation of anthracene as described above may be reacted to yield benzene. According to this invention, the anthraquinone may be converted to benzene by thermally cracking same, preferably in the presence of a catalyst, at a temperature of from about 425° to about 760° C. (797°–1400° F.), and in an inert atmosphere. Suitable catalysts include thermal cracking type catalysts. Examples of such catalysts include acid-treated clays, e.g., montmorillonite, bentonite, halloyrite, and the like; synthetic $SiO_2$-$Al_2O_3$ (10 to 25% $Al_2O_3$), synthetic $SiO_2$-MgO (25 to 35% MgO); and synthetic zeolites or molecular sieves and pellets or microspheres. A particular useful and preferred catalyst is a synthetic zeolite having a surface area of from about 100 to about 175 $m^2$/gm, preferably about 110–115 $m^2$/gm, a pore volume of from about 0.2 to about 0.6 cc/gm, preferably about 0.35 to 0.45 cc/gm, and an apparent bulk density of from about 0.5 to about 2.0 gm/cc, preferably about 0.70 to 0.80 gm/cc. It has also been found that hydrocracking catalysts cannot be used successfully in the cracking of anthraquinone to yield benzene, since these catalysts cause the hydrogenation of anthraquinone to anthracene.

In this thermal cracking step, it is important to use a temperature which is above about 425° C. At temperatures less than 425° C., the yield of benzene is substantially lower. More importantly, at temperatures below about 320° C., the cracking reaction will not proceed.

The thermal cracking step may be conducted at a gravimetric feed rate of from about 0.1 to about 8.0 grams anthraquinone/hour/grams catalyst, preferably from about 0.50 to about 2.0 grams anthraquinone/hour/grams catalyst.

The present invention is further illustrated by the following examples. It is emphasized that the following examples are for illustration purposes only and should not be construed as limiting the scope of the invention.

EXAMPLE 1

The following is an outline of the procedure which may be used in oxidizing the anthracene. The catalyst, e.g., ceric ammonium nitrate, which is a solid, is mixed with anthracene, which is also a solid. The anthracene-catalyst mixture is then dissolved in a suitable aqueous hydrocarbon solvent. Examples of such solvents include dimethyl sulfoxide, dimethylformamide, and tetrahydrofuran.

The solvent should be able to dissolve both the anthracene feed and the catalyst and may contain up to about 25% water. The solution containing the catalyst and anthracene is then reacted with a molecular oxygen containing gas, e.g. oxygen or air at a temperature of from about 65° C. to about 205° C. (149°–401° F.), preferably from about 82° to about 150° C. (180°–302° F.) until the reaction is complete, or when the catalyst has been completely consumed. The pressure at which the oxidation reaction is conducted does not seem to have much effect on the yield, and may be varied. Thus, atmospheric pressure is preferred for economic reasons, and pressure should not exceed about 100 psig.

After the oxidation reaction, the liquid mixture is poured into cold water (i.e. water at a temperature of from about 34° to about 45° F.) to precipitate the anthracene and anthraquinone. The precipitate is collected by filtration and dried to obtain a final product.

The above procedure is cited only as an example; other procedures may also be used. For example, the catalyst may be first deposited on a solid carrier and thereafter used to oxidize anthracene. By depositing the catalyst on a solid carrier, the separation of the products from the reaction mixture is much simplified.

By using the procedure outlined above, wherein the catalyst and anthracene were dissolved in a suitable solvent, the following runs were made. The feed was anthracene and the catalyst was ceric ammonium nitrate. All runs were made at atmospheric pressure. The experimental results are summarized in Table 1, and results are shown in FIG. 1.

As an explantion of the data shown in Example 1, it is hypothesized that the following reaction takes place.

TABLE 1

| | CATALYTIC OXIDATION OF ANTHRACENE | | | | | | | | | | | |
|---|---|---|---|---|---|---|---|---|---|---|---|---|
| | Run No. | | | | | | | | | | | |
| | 1-1 | 1-2 | 1-3 | 1-4 | 1-5 | 1-6 | 1-7 | 1-8 | 1-9 | 1-10 | 1-11 | 1-12 |
| Feed | ← | ← | ← | ← | Anthracene | → | → | → | → | → | → | → |
| Weight, gm | 2.68 | 2.68 | 2.68 | 0.67 | 0.67 | 0.67 | 2.68 | 2.68 | 2.68 | 2.68 | 2.68 | 2.68 |
| Catalyst | ← | ← | ← | Ceric | Ammonium | Nitrate | → | → | → | → | → | → |
| Weight, gm. | 4.02 | 4.02 | 4.02 | 4.02 | 4.02 | 4.02 | 4.02 | 4.02 | 4.02 | 4.02 | 4.02 | 4.02 |
| Organic Solvent | ← | ← | ← | Dimethylformamide | | | → | → | → | → | → | → |
| Temperature, °C. | 25 | 25 | 25 | 25 | 25 | 25 | 82 | 82 | 82 | 127 | 127 | 127 |
| Run time, minutes | 10 | 20 | 40 | 10 | 20 | 40 | 10 | 15 | 20 | 40 | 160 | 240 |
| Feed rate, gm.feed/hr/gm.catalyst | 4.00 | 2.00 | 1.00 | 1.00 | 0.50 | 0.25 | 1.00 | 0.67 | 0.50 | 1.00 | 0.25 | 0.17 |
| Conversion, mole % | 7.07 | 8.16 | 8.18 | 27.99 | 27.82 | 28.67 | 46.99 | 58.83 | 61.97 | 29.80 | 44.39 | 47.25 |
| Product Compositions, mole % | | | | | | | | | | | | |
| Anthracene | 92.93 | 91.84 | 91.83 | 72.01 | 72.18 | 71.33 | 53.01 | 41.17 | 38.03 | 70.20 | 55.61 | 52.75 |
| Unknown | 2.30 | 2.40 | 2.29 | — | — | — | — | — | — | — | — | — |
| 9,10-Anthraquinone | 4.77 | 5.76 | 5.89 | 27.99 | 27.82 | 28.67 | 46.99 | 52.58 | 54.68 | 26.69 | 41.59 | 41.59 |
| x,y-Anthraquinone | — | — | — | — | — | — | — | 6.25 | 7.29 | 3.11 | 2.80 | 5.66 |
| Mole Anthracene Converted | .1451 | .1675 | .1679 | .1436 | .1427 | .1471 | .2411 | .3019 | .3180 | .6116 | .9111 | .9698 |
| Mole Catalyst Used (Feed rate)$^{-1}$ | .25 | .50 | 1.00 | 1.00 | 2.00 | 4.00 | 1.00 | 1.50 | 2.00 | 1.00 | 4.00 | 6.00 |

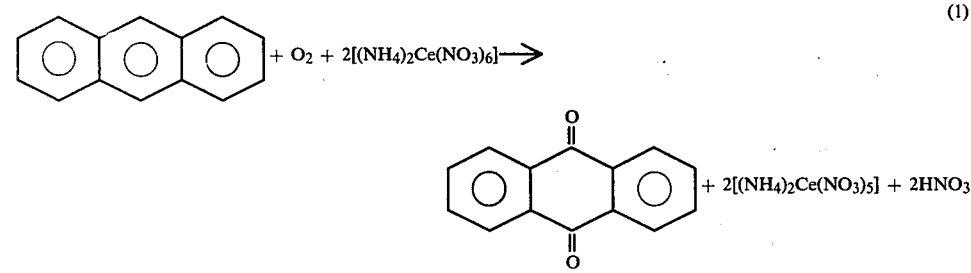

(1)

(2)

$$2HNO_3 + 2[(NH_4)_2Ce(NO_3)_5] + \tfrac{1}{2} O_2 \xrightarrow{\Delta}$$

-continued
$$2[(NH_4)_2Ce(NO_3)_6] + H_2O$$

The results obtained in Runs Nos. 1-10, 1-11, and 1-12 clearly support the above hypothesis. According to Equation (1), if the catalyst is not regenerated, the maximum ratio of anthracene which may be converted per mole of catalyst used is 0.50. However, in Run Nos. 1-10, 1-11 and 1-12, the ratios are 0.61, 0.91 and 0.97, respectively. Thus, carrying out the reaction at elevated temperatures is necessary to keep the level of catalyst deactivation at a minimum.

The above mechanism is offered merely as an explanation of the experimental results. Since other explanations are possible, the present inventor does not wish to be bound by the above explanation.

EXAMPLE 2

The procedure outlined in Example 1 was repeated using the organic solvent as the only solvent, i.e., no water was present in the solution mixture. The experimental conditions and results are summarized in Table 2.

The above reaction is a redox reaction wherein the catalyst is reduced to a nonactive oxidation state ($Ce^{+4} \rightarrow Ce^{+3}$). According to Equation 1, the catalyst is deactivated as the reaction proceeds.

It has been found that the catalyst deactivation can be avoided or alleviated by conducting the reaction at an elevated temperature, i.e., temperatures ranging from about 65° to about 205° C. (149° to 401° F.). At such elevated temperatures, the reduced catalyst is oxidized by the oxygen back to the active oxidation state ($Ce^{+3} \rightarrow Ce^{+4}$), according to Equation (2):

The results presented in Tables 1 and 2 are shown in FIG. 1. An analysis of FIG. 1 shows that at room temperature (i.e., about 77° F.) with about 25% water present in the reaction mixture, the ratio of mole anthracene converted/mole catalyst used is about 0.15. Without water in the reaction mixture, this ratio is about 0.35. At 82° C. (180° F.) the ratio for a waterless reaction mixture is about two times that of water-containing reaction mixture. The difference in this ratio at 127° C. (260° F.) is less pronounced, but still substantial.

Thus, from FIG. 1, it may be concluded that the anthracene oxidation reaction is much enhanced by carrying out the reaction at temperatures above room temperature. Furthermore, to obtain even better results, water should not be present in the reaction mixture.

EXAMPLE 3

The procedure outlined in Example 2 was repeated using a promotor of potassium chlorate ($KClO_3$) in the reaction solution. The experimental conditions and results are summarized in Table 3.

The results presented in Table 3 show that at 260° F. when the weight ratio of potassium chlorate to catalyst is varied from about 0.0 to 0.5, the yield of the isomerization product of 9, 10-anthraquinone decreases from about 18 mole % to about 1 mole %, while the ratio of moles of anthracene converted/moles of catalyst used increases from about 0.9 to about 1.1

Thus, from Table 3 it may be concluded that anthracene oxidation to produce 9, 10-anthraquinone is much enhanced by carrying out the reaction in the presence of potassium chlorate promoter.

converted to benzene by heating same in a nitrogen atmosphere at a temperature of 510° C. (950° F.) in the presence of a thermal cracking catalyst. Hydrogen was not used as a reactant. The catalyst used was a zeolite catalyst having the following characteristics:

| Type: | Synthetic Zeolite |
|---|---|
| Surface Area: | 113 m²/gm |
| Pore Volume: | 0.40 cc/gm |
| Apparent Bulk Density: | 0.74 gm/cc |

Experimental conditions and results are summarized in Table 4.

The results obtained in Run Nos. 4-1 and 4-3 show the effects of the presence of the catalyst. In Run No. 4-3, wherein no catalyst was used, the mole % of biphenyl in the products was 36.7%. In contrast, in Run No. 4-1, wherein a catalyst was used, mole % biphenyl was 42.7%. In addition, in Run No. 4-3, the total mole % of

TABLE 2
CATALYTIC OXIDATION OF ANTHRACENE WITHOUT WATER

| | Run No. | | | | | | | | | | |
|---|---|---|---|---|---|---|---|---|---|---|---|
| | 2-1 | 2-2 | 2-3 | 2-4 | 2-5 | 2-6 | 2-7 | 2-8 | 2-9 | 2-10 | 2-11 |
| Feed | ← | ← | ← | ← | Anthracene | → | → | → | → | → | → |
| Weight, gm | 0.67 | 0.67 | 0.67 | 2.68 | 2.68 | 2.68 | 2.68 | 2.68 | 2.68 | 2.68 | 2.68 |
| Catalyst | ← | ← | ← | Ceric Ammonium Nitrate | | | → | → | → | → | → |
| Weight, gm | 4.02 | 4.02 | 4.02 | 4.02 | 4.02 | 4.02 | 4.02 | 4.02 | 4.02 | 4.02 | 4.02 |
| Organic Solvent | ← | ← | ← | Dimethylformamide | | | → | → | → | → | → |
| Temperature, °C. | 25 | 25 | 25 | 82 | 82 | 82 | 82 | 82 | 127 | 127 | 127 |
| Run time, minutes | 10 | 15 | 20 | 10 | 20 | 40 | 80 | 160 | 40 | 160 | 240 |
| Feed rate, gm feed/hr/gm catalyst | 1.00 | 0.67 | 0.50 | 4.00 | 2.00 | 1.00 | 0.50 | 0.25 | 1.00 | 0.25 | 0.17 |
| Conversion, mole % | 73.97 | 67.67 | 66.22 | 21.93 | 28.46 | 30.02 | 27.35 | 32.03 | 44.22 | 53.41 | 52.74 |
| Product Compositions, mole % | | | | | | | | | | | |
| Anthracene | 26.03 | 32.33 | 33.78 | 78.09 | 71.54 | 69.98 | 72.65 | 67.97 | 55.78 | 46.59 | 47.26 |
| Unknown | — | — | — | — | — | — | — | — | — | — | — |
| 9,10-Anthraquinone | 59.70 | 56.87 | 55.16 | 11.99 | 13.64 | 14.26 | 14.36 | 15.71 | 21.22 | 25.22 | 24.72 |
| x,y-Antraquinone | 14.23 | 10.80 | 11.06 | 9.94 | 14.82 | 15.76 | 12.99 | 16.32 | 23.00 | 28.19 | 28.02 |
| Mole Anthracene Converted | | | | | | | | | | | |
| Mole Catalyst Used | .3795 | .3472 | .3398 | .4501 | .5841 | .6161 | .5613 | .6574 | .9076 | 1.0962 | 1.0825 |
| (Feed rate)$^{-1}$ | 1.00 | 1.50 | 2.00 | 0.25 | 0.50 | 1.00 | 2.00 | 4.00 | 1.00 | 4.00 | 6.00 |

TABLE 3
HOMOGENEOUS CATALYTIC OXIDATION OF ANTHRACENE WITH POTASSIUM CHLORATE PROMOTOR

| | Run No. | | | | | | | |
|---|---|---|---|---|---|---|---|---|
| | 3-1 | 3-2 | 3-3 | 3-4 | 3-5 | 3-6 | 3-7 | 3-8 |
| Feed Description: | | | | | | | | |
| Anthracene, wt.gm. | 2.68 | 2.68 | 2.68 | 2.68 | 2.68 | 2.68 | 2.68 | 2.68 |
| Catalyst, wt. gm. | 4.02 | 4.02 | 4.02 | 4.02 | 4.02 | 4.02 | 0.00 | 4.02 |
| $KClO_3$, wt. gm. | 0.26 | 0.52 | 1.04 | 1.30 | 1.56 | 1.82 | 2.08 | 2.08 |
| Solvent | Dimethyl Sulfoxide | | | | | | | |
| Operating Conditions | | | | | | | | |
| Temperature, °C. | 127 | 127 | 127 | 127 | 127 | 127 | 127 | 127 |
| Run Time, minutes | 40 | 40 | 40 | 40 | 40 | 40 | 40 | 40 |
| Feed rate, gm feed/hr/gm catalyst | 1.00 | 1.00 | 1.00 | 1.00 | 1.00 | 1.00 | — | 1.00 |
| Product Compositions, W % | | | | | | | | |
| Anthracene | 50.23 | 44.69 | 34.83 | 32.93 | 45.94 | 44.45 | 100.00 | 42.25 |
| 9,10-Anthraquinone | 30.03 | 38.65 | 53.70 | 58.22 | 51.55 | 52.90 | — | 56.25 |
| x,y-Anthraquinone | 19.74 | 16.66 | 11.46 | 8.85 | 2.51 | 2.65 | — | 1.50 |
| Product Compositions, mole % | | | | | | | | |
| Anthracene | 54.11 | 48.57 | 38.44 | 36.46 | 49.82 | 48.32 | 100.00 | 46.09 |
| 9,10-Anthraquinone | 27.69 | 35.94 | 50.73 | 55.16 | 47.85 | 49.21 | — | 52.51 |
| x,y-Anthraquinone | 18.20 | 15.49 | 10.83 | 8.38 | 2.33 | 2.47 | — | 1.40 |
| Conversion, mole % | 45.89 | 51.43 | 61.56 | 63.54 | 50.18 | 51.68 | 0.00 | 53.91 |
| Moles Anthracene Converted | 0.94 | 1.06 | 1.26 | 1.30 | 1.03 | 1.06 | 0.00 | 1.11 |
| Moles Catalyst Used | | | | | | | | |

EXAMPLE 4

In this example, 9, 10-anthraquinone was converted to biphenyl and then to benzene by catalytic thermal cracking. The 9, 10-anthraquinone was catalytically anthracene and fluorene was 36.0%, and for Run No. 4-1, 17.6%. As explained below, anthracene and fluorene are undesirable by-products, the amount of which should be kept at a minimum. Thus, the experimental results in Table 4 clearly indicate that the formation of undesirable by-products is much reduced when a catalyst is present in the reaction mixture, although the cracking reaction will proceed without a catalyst.

As an explanation of the results obtained in Example 4, the following if offered. However, it is emphasized that the inventor does not wish to be bound by such explanation since other explanations may be possible. It is believed that quinones of polynuclear aromatic hydrocarbons are converted to benzene in accordance with Equation (3).

EXAMPLE 6

Figure 3:
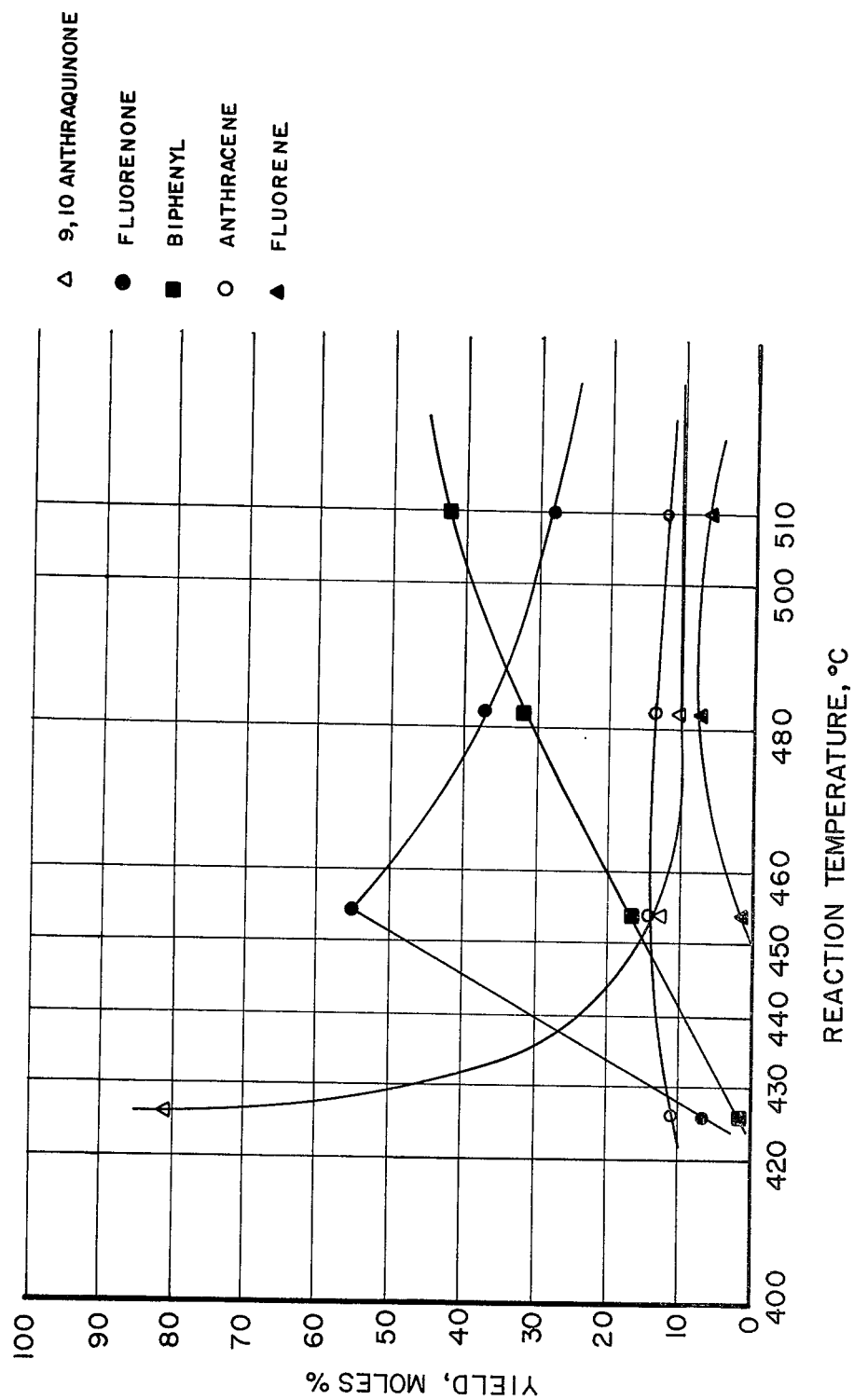
FIG. 3 illustrates the results of Example 6.

The procedure of Example 4 was repeated. The process conditions and results are summarized in Table 6. Some of the results in Table 6 are shown in FIG. 3 wherein the yield in mole % is plotted against temperature. FIG. 3 shows that the yield of fluorenone passes through a maximum at about 450° C. (842° F.) when the reaction temperature is raised from 425° to 510° C. (800°–950° F.).

TABLE 4
CRACKING ANTHRAQUINONE TO BENZENE

| | Run No. | | |
|---|---|---|---|
| | 4-1 | 4-2 | 4-3 |
| Operating Conditions | | | |
| Atmosphere | Nitrogen | Nitrogen | Nitrogen |
| Temperature, °C. | 510 | 510 | 510 |
| Run Time, minutes | 70 | 70 | 70 |
| Feed | Anthraquinone | Anthracene | Anthraquinone |
| Catalyst | Zeolite | Zeolite | None |
| Gravimetric Feed Rate, Gm Feed/Hr/Gm Cat. | 2.57 | 2.57 | —* |
| Conversion, Mole % | 88.4 | 17.9 | 91.7 |
| Product Composition, Mole % | | | |
| Anthraquinone | 11.6 | — | 8.3 |
| Anthracene | 11.7 | 82.1 | 25.6 |
| Fluorenone | 28.0 | — | 19.0 |
| 1,2,3,4-tetrahydroanthracene | — | 0.9 | — |
| 9,10-dihydroanthracene | — | 3.2 | — |
| Octahydroanthracene | — | 2.2 | — |
| Fluorene | 6.0 | — | 10.4 |
| Biphenyl | 42.7 | — | 36.7 |
| Naphthalenes | — | 11.6 | — |

*Feed rate without catalyst was 12.85 gm feed/hr.

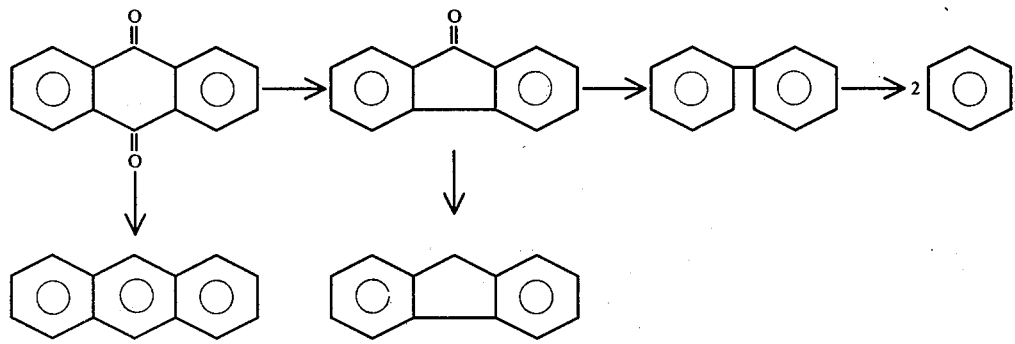

(3)

Since Run No. 4-2 shows that anthracene cannot be converted to biphenyl, it must be assumed that the anthracene formed in Run Nos. 4-1 and 4-3 is an undesirable by-product.

EXAMPLE 5

Figure 2:
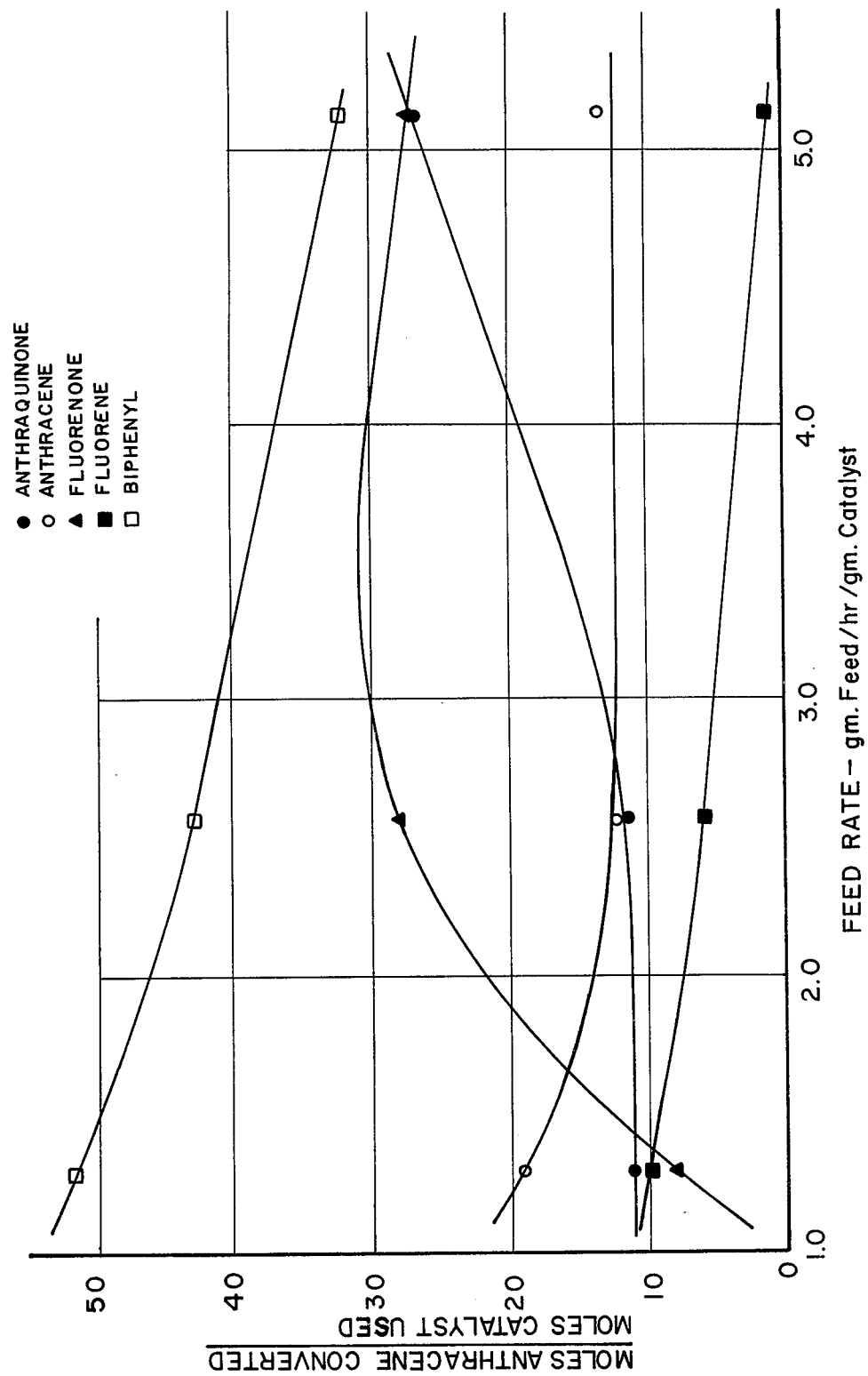
FIG. 2 is a similar graph which illustrates the results of Example 5.

The procedure described in Example 4 was repeated. The experimental conditions and results are summarized in Table 5. Some of the results are presented in FIG. 2, wherein the yields in mole % are plotted as a function of the gravimetric feed rate. The data in FIG. 2 show that fluorenone was formed as an intermediate product. Its concentration first increased with increasing feed rate and then decreased with further increases in the feed rate, while the biphenyl yield decreased with increasing feed rates. These results substantiate the reaction scheme represented by Equation (3).

TABLE 5
CATALYTIC CRACKING ANTHRAQUINONE TO BENZENE

| | Run No. | | |
|---|---|---|---|
| | 5-1 | 5-2 | 5-3 |
| Catalyst | Zeolite | Zeolite | Zeolite |
| Catalyst Wt,Gm. | 5.0 | 5.0 | 5.0 |
| Feed | 9,10-Anthraquinone | | |
| Feed Wt, Gm | 15 | 15 | 15 |
| Operating Conditions | | | |
| Temperature, °C. | 510 | 510 | 510 |
| Run Time, minutes | 35 | 70 | 140 |
| Feed rate, gm feed/hr/gm catalyst | 5.14 | 2.57 | 1.29 |
| Conversion, Mole % | 73.41 | 88.4 | 88.9 |
| Product Composition, W % | | | |
| Anthraquinone | 30.95 | 14.1 | 12.8 |
| Anthracene | 13.16 | 12.2 | 20.1 |
| Fluorenone | 27.24 | 29.5 | 8.8 |
| Fluorene | 1.14 | 5.4 | 9.9 |
| Biphenyl | 27.51 | 38.4 | 47.4 |

TABLE 5-continued

CATALYTIC CRACKING ANTHRAQUINONE TO BENZENE

| | Run No. | | |
|---|---|---|---|
| | 5-1 | 5-2 | 5-3 |
| Product Composition, Mole % | | | |
| Anthraquinone | 26.59 | 11.6 | 11.1 |
| Anthracene | 13.21 | 11.7 | 19.0 |
| Fluorenone | 27.04 | 28.0 | 8.2 |
| Fluorene | 1.23 | 6.0 | 10.0 |
| Biphenyl | 31.92 | 42.7 | 51.7 |

TABLE 6

CATALYTIC CRACKING ANTHRAQUINONE TO BENZENE

| | Run No. | | | | | | | | |
|---|---|---|---|---|---|---|---|---|---|
| | 6-1 | 6-2 | 6-3 | 6-4 | 6-5 | 6-6 | 6-7 | 6-8 | 6-9 |
| Catalyst | Zeolite | Zeolite | Zeolite | Zeolite | Zeolite | Zeolite | Zeolite | Zeolite | Zeolite |
| Catalyst Weight, Gm. | 5.0 | 5.0 | 5.0 | 5.0 | 5.0 | 7.5 | 2.5 | 5.0 | 7.5 |
| Feed | ← | ← | ← | 9,10-Anthraquinone | | | → | → | → |
| Feed Weight, Gm. | 15 | 15 | 15 | 15 | 15 | 15 | 15 | 15 | 15 |
| Operating Conditions | | | | | | | | | |
| Temperature, °C. | 510 | 482 | 454 | 427 | 510 | 510 | 515 | 510 | 454 |
| Run Time, minutes | 70 | 70 | 70 | 70 | 140 | 70 | 70 | 35 | 70 |
| Feed Rate, gm feed/hr/gm catalyst | 2.57 | 2.57 | 2.57 | 2.57 | 1.29 | 1.71 | 5.14 | 5.14 | 1.71 |
| Product Compositions, W % | | | | | | | | | |
| Anthraquinone | 14.1 | 11.9 | 15.2 | 83.2 | 13.8 | 27.1 | 33.1 | 31.0 | 79.1 |
| Anthracene | 12.2 | 22.3 | 13.5 | 9.5 | 20.1 | 8.5 | 13.2 | 13.2 | 3.5 |
| Fluorenone | 29.5 | 34.2 | 55.7 | 6.0 | 8.8 | 14.1 | 24.3 | 27.2 | 10.9 |
| Fluorene | 5.8 | 1.5 | 1.3 | 0.0 | 9.9 | 3.9 | 4.0 | 1.1 | 0.0 |
| Biphenyl | 38.4 | 30.1 | 14.3 | 1.3 | 47.4 | 46.4 | 25.4 | 27.5 | 6.5 |
| Product Compositions, Mole % | | | | | | | | | |
| Anthraquinone | 11.6 | 10.6 | 13.1 | 80.8 | 11.1 | 22.4 | 28.6 | 26.6 | 75.6 |
| Anthracene | 11.7 | 12.6 | 13.6 | 10.8 | 19.0 | 8.2 | 13.2 | 13.2 | 3.9 |
| Fluorenone | 28.0 | 37.4 | 55.3 | 6.7 | 8.2 | 13.5 | 24.2 | 27.1 | 12.1 |
| Fluorene | 6.0 | 7.3 | 1.4 | 0.0 | 10.0 | 4.0 | 4.4 | 1.2 | 0.0 |
| Biphenyl | 42.7 | 32.1 | 16.6 | 1.7 | 51.7 | 51.9 | 29.6 | 31.9 | 8.4 |
| Conversion, Mole % | 88.4 | 89.4 | 86.9 | 19.2 | 88.9 | 77.6 | 71.4 | 73.4 | 24.4 |

EXAMPLE 7

The procedure of Example 4 was repeated, with the exception that biphenyl was used as the feed. The products were subjected to analysis by gas chromatography. The results are shown in FIG. 4, which clearly indicate that benzene can be formed from biphenyl under the thermal cracking conditions of Example 4.

As is apparent from the above description, the present invention provides a method of converting anthracene to anthraquinone, which is in turn converted to biphenyl, which is then converted to benzene. The invention may also be used to convert the anthracene present in coal-derived hydrocarbon liquids to benzene.

What is claimed is:

1. A process of producing benzene from anthracene comprising:
   (a) oxidizing the anthracene to anthraquinone by reacting the anthracene with a molecular oxygen-containing gas in the presence of a catalyst selected from the group consisting of ceric ammonium nitrate, ceric nitrate, ceric ammonium sulfate, ceric sulfate, ceric perchlorate or other compounds of $Ce^{+4}$, and in the presence of a promoter, the reaction being carried out at a temperature of from about 65° to about 205° C. in an essentially water-free environment;
   (b) thermally cracking the anthraquinone obtained in (a) at a temperature of from about 425° to about 760° C., and in an inert atmosphere to form benzene.

2. The process of claim 1 wherein the catalyst in (a) is ceric ammonium nitrate.

3. The process of claim 1 wherein the molecular oxygen-containing gas is air.

4. The process of claim 1 wherein the promoter in (a) is potassium chlorate.

5. The process of claim 1 wherein the reaction step (a) is conducted at a gravimetric feed rate of from about 0.2 to about 2.5 gm anthracene/hour/gm catalyst.

6. The process of claim 1 wherein step (b) is conducted in the presence of a thermal cracking catalyst selected from the group consisting of synthetic zeolites, molecular sieves, and synthetic $SiO_2$-$Al_2O_3$, synthetic $SiO_2$-MgO.

7. The process of claim 6 wherein step (b) is conducted at a gravimetric feed rate of from about 0.1 to about 8.0 gm anthraquinone/hour/gm catalyst.

8. The process of claim 6 wherein the catalyst in step (b) is zeolite having a surface area of from about 100 to about 175 $m^2$/gm, a pore volume of from about 0.2 to about 0.6 cc/gm and an apparent bulk density of from about 0.5 to about 2.0 gm/cc.

9. A process of producing benzene from anthracene comprising:
   (a) oxidizing the anthracene to anthraquinone by reacting the anthracene with air in the presence of a catalyst consisting of essentially ceric ammonium nitrate, and in the presence of a promoter consisting of substantially potassium chlorate, the reaction being carried out at a temperature of from about 65° to about 205° C. in an essentially water-free environment and at a gravimetric feed rate of about 0.2 to 2.5 gm anthracene/hr/gm catalyst;
   (b) thermally cracking the anthraquinone obtained in (a) in the presence of synthetic zeolite cracking catalyst at a temperature of from about 425° to about 750° C., and in an inert atmosphere at gravimetric feed rate of about 0.1 to 8.0 gm anthraquinone/hr/gm catalyst to form benzene.

10. A process of producing 9,10-anthraquinone comprising reacting anthracene with a molecular oxygen-containing gas at a temperature of from about 65° to about 205° C. (149°–401° F.) in the presence of a catalyst selected from the group consisting of ceric ammonium nitrate, ceric nitrate, ceric ammonium sulfate, ceric sulfate, ceric perchlorate or other compounds of $Ce^{+4}$, the reaction being conducted in an essentially water-free environment.

11. The process of claim 10 wherein the molecular oxygen-containing gas is air.

12. The process of claim 10 wherein the catalyst is ceric ammonium nitrate.

13. The process of claim 12 wherein the gravimetric feed rate is from about 0.2 to about 2.5 gm anthracene/hour/gm catalyst.

14. A process of producing 9, 10-anthraquinone comprising reacting anthracene with air at a temperature of from about 65° to about 205° C. (149°–401° F.) in the presence of a catalyst consisting essentially of ceric ammonium nitrate, the reaction being conducted in an essentially water-free environment and at a gravimetric feed rate from about 0.2 to about 2.5 gm anthraquinone/hour/gm catalyst.

15. A process of producing benzene from 9, 10-anthraquinone comprising thermally cracking 9, 10-anthraquinone at a temperature of from about 425° to about 760° C. (797°–1400° F.) and in an inert atmosphere.

16. The process of claim 15 wherein the thermal cracking is conducted in the presence of a thermal cracking catalyst selected from the group consisting of acid-treated clays, and synthetic zeolites, synthetic $SiO_2Al_2O_3$, synthetic $SiO_2$-MgO.

17. The process of claim 16 wherein the reaction is carried out at a gravimetric feed rate of from about 0.1 to 8.0 gm anthraquinone/hour/gm catalyst.

18. The process of claim 16 wherein the catalyst is synthetic zeolite having a surface area of from about 100 to about 175 m²gm; a pore volume of from 0.2 to about 0.6 cc/gm, and an apparent bulk density of from about 0.5 to about 2.0 gm/cc.

19. A process of producing benzene from 9, 10-anthraquinone comprising thermally cracking 9, 10-anthraquinone at a temperature of from about 425° to about 760° C. (797°–1400° F.) in an inert atmosphere in the presence of a thermal cracking catalyst consisting essentially of synthetic zeolites and wherein the reaction is carried out at a gravimetric feed rate of from about 0.1 to 8.0 gm anthraquinone/hour/gm catalyst.

20. A process of producing benzene from a mixture of polynuclear aromatic compounds having a boiling temperature ranging from about 170° to about 380° C. (338°–716° F.), comprising:
 (a) oxidizing the mixture of polynuclear aromatic compounds by reacting the mixture with a molecular oxygen-containing gas in the presence of a catalyst selected from the group consisting of ceric ammonium nitrate, ceric nitrate, ceric ammonium sulfate, ceric sulfate, ceric perchlorate or other compounds of $Ce^{+4}$ and a promoter material, the reaction being carried out at a temperature of from about 65° to about 205° C. and in an essentially water-free environment,
 (b) thermally cracking the product of (a) at a temperature of from about 425° to about 760° C. and in an inert atmosphere to produce benzene.

21. The process of claim 20 wherein the catalyst in (a) is ceric ammonium nitrate.

22. The process of claim 20 wherein the promoter in (a) is substantially potassium chlorate.

23. The process of claim 20 wherein the molecular oxygen-containing gas is air.

24. The process of claim 20 wherein the mixture of polynuclear aromatic compound comprises coal derived liquids boiling between about 170° and 380° C.

25. The process of claim 20 wherein the reaction of (a) is conducted at a gravimetric feed rate of from about 0.2 to about 2.5 gm feed/hour/gm catalyst.

26. The process of claim 20 wherein step (b) is conducted in the presence of a thermal cracking catalyst selected from the group consisting of acid-treated clays, molecular sieves, synthetic zeolites, synthetic $SiO_2$-$Al_2O_3$, and synthetic $SiO_2$-MgO.

27. The process of claim 26 wherein the reaction in (b) is conducted at a gravimetric feed rate of from about 0.1 to about 8.0 gm feed/hour/gm catalyst.

28. The process of claim 26 wherein the catalyst in (b) is synthetic zeolite having a surface area of from about 100 to about 175 m²/gm, a pore volume of from about 0.2 to about 0.6 cc/gm and an apparent bulk density from about 0.5 to about 2.0 gm/cc.

29. A process of producing benzene from a mixture of polynuclear aromatic compounds derived from coal and having a boiling temperature ranging from about 170° to about 380° C. (338°–716° F.), comprising:
 (a) oxidizing the mixture of polynuclear aromatic compounds by reacting the mixture with air in the presence of a catalyst consisting essentially of ceric ammonium nitrate, and a promoter material of substantially potassium chlorate, the reaction being carried out at a temperature of from about 65° to about 205° C. in an essentially water-free environment, and at a gravimetric feed rate of from about 0.2 to about 2.5 gm feed/hour/gm catalyst;
 (b) thermally cracking the product of (a) in the presence of a synthetic zeolite thermal cracking catalyst at a temperature of from about 425° to about 760° C. in an inert atmosphere at a gravimetric feed rate of from about 0.1 to 8.0 gm feed/hr/gm catalyst to produce benzene.

* * * * *